United States Patent
Lineaweaver et al.

(10) Patent No.: US 8,825,168 B2
(45) Date of Patent: *Sep. 2, 2014

(54) USING A GENETIC ALGORITHM EMPLOYING DYNAMIC MUTATION

(75) Inventors: Sean Lineaweaver, Parker, CO (US); Gregory H. Wakefield, Ann Arbor, MI (US)

(73) Assignee: Cochlear Limited, Macquarie University, NSW (AU)

( * ) Notice: Subject to any disclaimer, the term of this patent is extended or adjusted under 35 U.S.C. 154(b) by 697 days.

This patent is subject to a terminal disclaimer.

(21) Appl. No.: 12/557,218

(22) Filed: Sep. 10, 2009

(65) Prior Publication Data

US 2011/0060383 A1   Mar. 10, 2011

(51) Int. Cl.
*A61N 1/00* (2006.01)
(52) U.S. Cl.
USPC ............ 607/55; 607/56; 607/57; 607/2
(58) Field of Classification Search
CPC .................. A61N 1/36032; A61F 11/045
USPC ............... 607/57, 136, 137, 2, 59, 55, 56
See application file for complete search history.

(56) References Cited

U.S. PATENT DOCUMENTS

| | | | |
|---|---|---|---|
| 4,532,930 A | 8/1985 | Crosby et al. | |
| 4,953,112 A | 8/1990 | Widin et al. | |
| 5,095,904 A | 3/1992 | Seligman et al. | |
| 5,277,694 A | 1/1994 | Leysieffer et al. | |
| 5,626,629 A | 5/1997 | Faltys et al. | |
| 6,157,861 A | 12/2000 | Faltys et al. | |
| 6,272,479 B1 | 8/2001 | Farry et al. | |
| 6,697,674 B2 | 2/2004 | Leysieffer | |
| 7,343,021 B2 | 3/2008 | Takagi et al. | |
| 2002/0176584 A1 | 11/2002 | Kates | |
| 2003/0133578 A1 | 7/2003 | Durant | |
| 2004/0181266 A1* | 9/2004 | Wakefield et al. | 607/57 |
| 2005/0107845 A1* | 5/2005 | Wakefield et al. | 607/57 |
| 2005/0129262 A1 | 6/2005 | Dillon et al. | |
| 2008/0165978 A1 | 7/2008 | Cronin et al. | |

(Continued)

FOREIGN PATENT DOCUMENTS

| | | |
|---|---|---|
| JP | 09-325773 | 12/1997 |
| JP | 11-513539 | 11/1999 |
| JP | 2003-6171 | 1/2003 |
| WO | WO 2007/090243 | 8/2007 |

OTHER PUBLICATIONS

International Search Report for PCT/US04/07400 mailed Aug. 27, 2004.
Written Opinion for PCT/US04/07400 dated Aug. 27, 2004.

(Continued)

*Primary Examiner* — Niketa Patel
*Assistant Examiner* — William Levicky
(74) *Attorney, Agent, or Firm* — K&L Gates LLP

(57) ABSTRACT

Apparatus and method for at least partially fitting a medical implant system to a patient is described. These apparatuses and methods comprise using a dynamic mutation rate. This genetic algorithm may comprise generating successive generations of child populations. In executing the genetic algorithm, children may undergo mutations based on a mutation rate. This mutation rate may be dynamic and be based on the characteristics of the children in the generation. Additionally, values may be frozen during execution of the genetic algorithm if the likelihood that the value has converged on a particular value exceeds a threshold.

15 Claims, 6 Drawing Sheets

(56) References Cited

U.S. PATENT DOCUMENTS

| | | | |
|---|---|---|---|
| 2010/0152813 | A1 | 6/2010 | Lineaweaver et al. |
| 2010/0280307 | A1 | 11/2010 | Lineaweaver et al. |
| 2011/0060384 | A1 | 3/2011 | Lineaweaver |
| 2011/0060702 | A1 | 3/2011 | Lineaweaver |
| 2012/0116480 | A1 | 5/2012 | Tsay et al. |

OTHER PUBLICATIONS

Forrest, Stephanie, "Genetic Algorithms: Principles of Natural Selection Applied to Computation," Science, Aug. 13, 1993, vol. 261 (5123), pp. 872-878.

Takagi, Hideyuki, "Interactive Evolutionary Computation: Fusion of the Capabilities of EC Optimization and Human Evaluation," Proceedings of the IEEE, Sep. 2001, vol. 89, No. 9, pp. 1275-1296.

Hideyuki Takagi, IEC-based Hearing Aid Fitting, IEEE SM C' 99 Conference Proceedings, Oct. 1999, vol. 3, 657-662 (6 pages).

International Search Report for International Application No. PCT/IB2010/054105 mailed Jun. 14, 2011 (5 pages).

European Official Communication for European Application No. 04 719 779.3 mailed Apr. 20, 2011 (3 pages).

Canadian Intellectual Property Office, "Office Action," issued in connection with Canadian Patent Application Serial No. 2,518,997, on Apr. 16, 2010 (2 pages).

Skinner, et al., "Speech Recognition with the Nucleus 24 SPEAK, ACE, and CIS Speech Coding Strategies in newly Implanted Adults," Ear & Hearing, vol. 23, No. 3, 208-223, (Jun. 2002) (17 pages).

Skinner, et al., "Nucleus 24 Advanced Encoder Conversion Study: Performance versus Preference," Ear & Hearing, vol. 23, No. 18, 3S-7S, (Feb. 2002) (16 pages).

Wakefield, et al., "Recipient-Directed Design of Speech processor MAPs," in R.T. Miyamoto, ed., Cochlear Implants, Elsevier, International Congress Series, 1273 178-182 (2004) (5 pages).

Wakefield, et al., "Genetic Algorithms for Adaptive Psychopysical Procedures: Recipient-Directed Design of Speech-Processor MAPs," Ear & Hearing, 52S-72S, (Aug. 2005) (16 pages).

Japanese Office Action for Japanese Application No. 2006-507068 mailed on Jun. 1, 2010 along with English translation (4 pages).

Japanese Office Action for Japanese Application No. 2006-507068 mailed on Mar. 8, 2011 along with English translation (3 pages).

Japanese Office Action for Japanese Application No. 2006-507068 mailed on Oct. 18, 2011 along with English translation (5 pages).

Trautmann et al., A Convergence Criterion for Multiobjective Evolutionary Algorithms Based on Systemic Statistical Testing, 2008, Springer-Verlag, pp. 825-836 (12 pages).

Rudolph, Covergence Analysis of Canonical Genetic Algorithms, 1994, IEEE, pp. 96-101 (6 pages).

* cited by examiner

USING A GENETIC ALGORITHM EMPLOYING DYNAMIC MUTATION

CROSS-REFERENCE TO RELATED APPLICATIONS

This application is related to PCT Application No. PCT/US2004/007400, U.S. Pat. Nos. 4,532,930, 5,277,694, 6,123,660, 6,162,169, 6,537,200, 6,565,503, 6,575,894, and 6,697,674, 6,879,860, U.S. patent application Ser. No. 10/963,594, entitled "Using a Genetic Algorithm to Fit a Cochlear implant System to a Patient," filed Oct. 13, 2004, U.S. patent application Ser. No.: 12/557,233, entitled "Using a Genetic Algorithm Employing an Expedited Convergence Algorithm," filed concurrent with the present application, and U.S. patent application Ser No.: 12/557,208, entitled "Using a Genetic Algorithm to Fit a Medical Implant System to a Patient," filed concurrent with the present application. The entire disclosure and contents of the above patents are hereby incorporated by reference herein.

BACKGROUND

1. Field of the Invention

The present invention relates generally to stimulating medical devices, and more particularly, to fitting a stimulating medical device.

2. Related Art

Many medical devices have structural and/or functional features which are to be adjusted for an individual patient. The process by which a medical device is tailored or customized for the specific needs of a patient is commonly referred to as fitting. One type of medical device which is typically fitted to individual recipients is a cochlear implant system.

Cochlear implant systems provide the benefit of hearing to individuals suffering from severe to profound hearing loss. Hearing loss in such individuals is often due to the absence or destruction of the hair cells in the cochlea which transduce acoustic signals into nerve impulses. Cochlear implant systems essentially simulate the auditory nerves by directly delivering electrical stimulation to the auditory nerve fibers. This causes the brain to perceive a hearing sensation resembling the natural hearing sensation normally delivered by the auditory nerve. Examples of cochlear implant systems are described, by way of example, in U.S. Pat. Nos. 4,532,930, 6,537,200, 6,565,503, 6,575,894, and 6,697,674, among others.

Conventional cochlear implant systems commonly include an external assembly directly or indirectly attached to the body of the patient (sometimes referred to herein as the recipient), and an internal assembly which is implanted in the patient. The external assembly typically comprises one or more microphones for detecting sound, a speech processing unit that converts detected sound into an electrical coded signal, a power source, and an external transcutaneous transfer coil. The internal assembly typically comprises an internal transcutaneous transfer coil, a stimulator unit located within a recess of the temporal bone of the recipient, and an electrode array positioned in the recipient's cochlea. Completely implantable cochlear implant systems having functionally similar components are under development.

In addition to providing electrical stimulation, some cochlear implant systems also include a mechanical stimulation mode of operation. Such so called mixed-mode systems offer rehabilitation by mechanically stimulating a portion of a patient's auditory pathway, either acoustically or physically. For example, there have been approaches to offer rehabilitation with conventional hearing aids via the application of an amplified acoustic signal to the external auditory canal, or by physically stimulating an ossicle of the middle ear or the inner ear via mechanical or hydromechanical stimulation.

Modern cochlear implant systems provide a wide variety of fitting options that can be customized for an individual patient. Because patients are heterogeneous, each patient requires a different set of parameters to maximize speech reception and patient satisfaction. The task of the clinical professional, usually an audiologist, is to select a set of parameters, commonly referred to as a parameter map or, more simply, a MAP, that will provide the best possible sound reception for an individual patient. Because there may be thousands of possible parameter maps, it is impractical for a patient to experience all of the alternatives and to evaluate the performance of each alternative. Nor is it possible to identify an optimal parameter map by prescription based on a limited set of measurements as is, for example, the case in fitting eyeglasses. Because parameters of cochlear implant systems often interact non-linearly and non-monotonically, it is also not possible to sequentially optimize parameters one at a time, adjusting each in succession to its optimal value.

As a result, clinicians have adopted a variety of approaches for fitting the cochlear implant systems to a patient. Some simply set the parameters to default values regardless of the individual patients. Others adopt preferred parameter maps, which they believe are good, if not best, for many or most patients. The preferences may be based on personal experience, published performance data, or intuition. Some clinicians evaluate a limited set of alternatives adjusting individual parameters based upon measured perceptual limitations and inferred relationships among the parameters. These approaches are time consuming, costly, and unreliable, and typically fail to achieve the optimal outcome for individual patients.

SUMMARY

In one aspect of the present invention there is provided a method for at least partially fitting a medical implant system to a patient comprising: executing a genetic algorithm to select a determined value set comprising values for a plurality of fitting parameters, the genetic algorithm comprising: presenting signals processed by a plurality of value sets to the patient using the medical implant system; receiving patient feedback in response to signals processed by the plurality of value sets; selecting, based on the patient feedback, one or more of the value sets; generating a successive generation of value sets using said selected one or more value sets; selecting a mutation rate based on at least one of the value sets for the successive generation; and mutating at least a portion of at least one value set for the successive generation using the selected mutation rate; and providing said determined value set to said medical implant system for use in providing stimulation to the patient.

In another aspect of the present invention, there is provided a system for at least partially fitting a medical implant system to a patient comprising: a processor configured to execute a genetic algorithm to select a determined value set comprising values for a plurality of fitting parameters, wherein the processor in executing the genetic algorithm is configured to present signals processed by a plurality of value sets to the patient using the medical implant system, receive patient feedback in response to the signals processed by the plurality of value sets, select, based on the patient feedback, one or more of the value sets, generate a successive generation of value sets using said selected one or more value sets, select a mutation rate based on at least one of the value sets for the successive generation, and mutate at least a portion of at least one value set for the successive generation using the selected mutation rate; and an interface configured to provide at least one of the value sets to the medical implant system for use by the medical implant system in providing stimulation to the patient.

In another aspect of the present invention, there is provided a system for at least partially fitting a medical implant system to a patient comprising: means for executing a genetic algorithm to select a determined value set comprising values for a plurality of fitting parameters, the genetic algorithm comprising: means for presenting signals processed by a plurality of value sets to the patient using the medical implant system; means for receiving patient feedback in response to the signals processed by the plurality of value sets; means for selecting, based on the patient feedback, one or more of the value sets; means for generating a successive generation of value sets using said selected one or more value sets; means for selecting a mutation rate based on at least one of the value sets for the successive generation; and means for mutating at least a portion of at least one value set for the successive generation using the selected mutation rate; and means for providing said determined value set to said medical implant system for use in providing stimulation to the patient.

In yet another aspect of the present invention, there is provided a computer-readable media encoded with instructions operative to cause a computer to perform a method for at least partially fitting a medical implant system to a patient, the method comprising: executing a genetic algorithm to select a determined value set comprising values for a plurality of fitting parameters, the genetic algorithm comprising: presenting signals processed by a plurality of value sets to the patient using the medical implant system; receiving patient feedback in response to the signals processed by the plurality of value sets; selecting, based on the patient feedback, one or more of the value sets; generating a successive generation of value sets using said selected one or more value sets; selecting a mutation rate based on at least on of the value sets for the successive generation; and mutating at least a portion of at least one value set for the successive generation using the selected mutation rate; and providing said determined value set to said medical implant system for use in providing stimulation to the patient.

BRIEF DESCRIPTION OF THE DRAWINGS

Embodiments of the present invention are described below with reference to the attached drawings, in which.

DETAILED DESCRIPTION

Aspects of the present invention are generally directed to the use of a genetic algorithm in fitting a stimulating medical device. In an embodiment, a fitting system may mutate generated child MAPs in accordance with a dynamic mutation rate. The mutation rate applied by the fitting system may vary based on, for example, the homogeneity of child MAPs generated in a particular generation. An exemplary embodiment of a genetic algorithm using a dynamic mutation rate will be discussed in more detail below after a presentation of an exemplary environment for implementation of such an algorithm.

Figure 1:
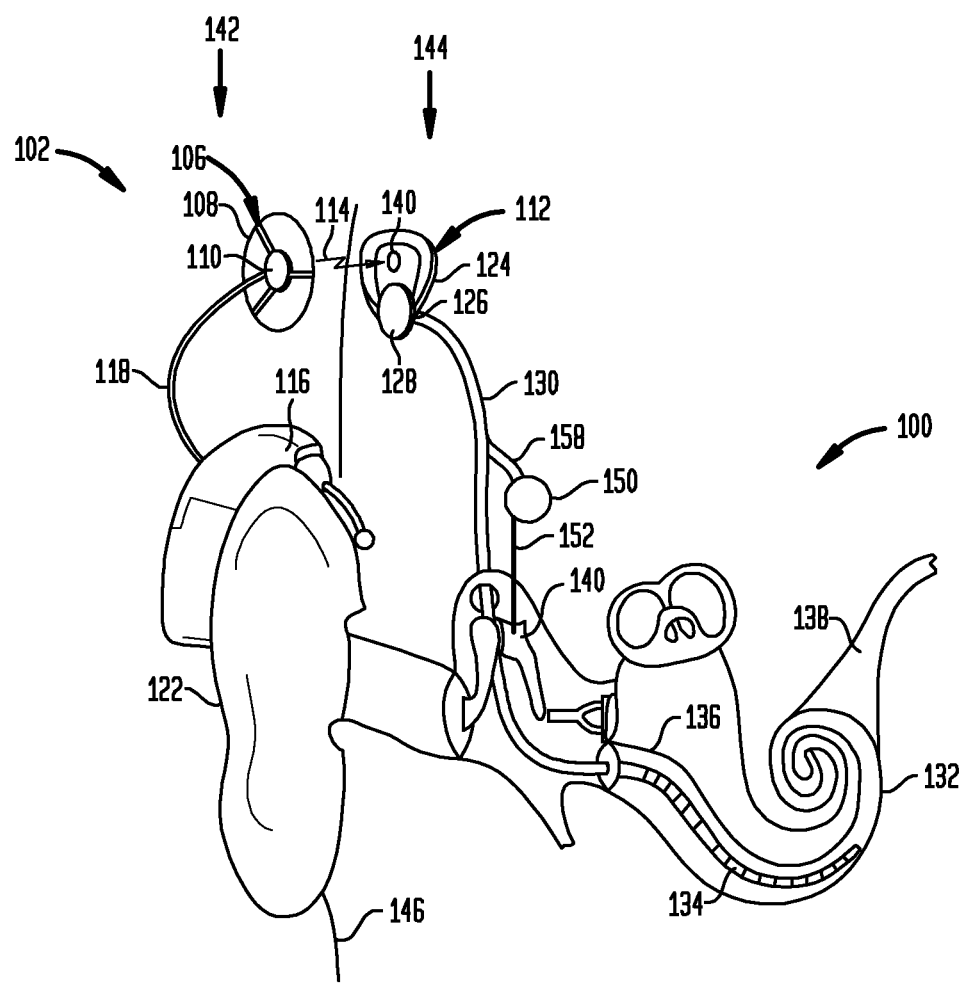
FIG. 1 is a schematic diagram of an exemplary cochlear implant system which may be fitted to an individual patient in accordance with an embodiment.

FIG. 1 is a schematic diagram of an exemplary cochlear implant system 100 which may be fitted to an individual patient in accordance with embodiments of the present invention. This embodiment of cochlear implant system 100 has single- and mixed-mode operational capabilities. With regard to an electrical stimulation mode of operation, cochlear implant system 100 provides direct electrical stimulation of auditory nerve cells to bypass absent or defective hair cells that normally transduce acoustic vibrations into neural activity. In this illustrative embodiment, cochlear implant system 100 comprises external component assembly 142 which is directly or indirectly attached to the body of the patient, and an internal component assembly 144 which is temporarily or permanently implanted in a patient. External assembly 142 typically comprises at least one audio pickup device such as a microphone (not shown) for detecting sounds, a speech processing unit 116 that converts the detected sounds into a coded signal, a power source (not shown), and an external transmitter unit 106. External transmitter unit 106 comprises an external coil 108, and, preferably, a magnet 110 secured directly or indirectly to external coil 108. Speech processor 116 processes the output of the audio pickup devices that may be positioned, for example, by the ear 122 of the recipient. Speech processor 116 generates stimulation signals which are provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to basilar membrane 136 thereby stimulating auditory nerve 138. Typically, the electrodes differentially activate auditory neurons that normally encode differential pitches of sound.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone molding (not shown). In use, implantable receiver unit 112 may be positioned, for example, in a recess of the temporal bone adjacent ear 122 of the recipient.

Regarding the mechanical mode of operation, cochlear implant system 100 provides, in this illustrative embodiment, direct mechanical stimulation to the patient's middle ear.

Electromechanical transducer 150 is coupled to the middle ear or inner ear using any technique now or later developed. Transducer 150 stimulates the impaired inner ear by direct mechanical coupling via coupling element 152 to a middle ear ossicle or via an air gap coupling for implantable transducers which are electromagnetic, for example. In this illustrative embodiment, electromechanical transducer 150 is coupled to incus 140. One example of transducer 150 is described in U.S. Pat. No. 5,277,694 which is hereby incorporated by reference herein. In the embodiment of a hermetically tight transducer described therein, a housing wall of the transducer is designed as a vibrating membrane which, together with a piezoelectric ceramic wafer applied to the inside thereof, comprises an electromechanically active composite element, the mechanical vibrations of which are transmitted to the ossicular chain via a coupling rod 152 permanently attached to the outside of the membrane. Optionally, coupling rod 152 can be attached to the membrane via a coupling element which is connected to the coupling rod. Alternatively, transducer 150 can be implemented as described in U.S. Pat. No. 6,123,660 which is hereby incorporated by reference. In such an embodiment, a permanent magnet is attached to the inside of the piezoelectric ceramic wafer to interact with an electromagnetic coil, such as an electromagnetic transducer. Such a combined piezoelectric-electromagnetic transducer is advantageous in particular with respect to a wide frequency band and achieving relatively high vibration amplitudes with comparatively small supplied energy.

In an alternative embodiment, transducer 150 can be an electromagnetic transducer arrangement as is described in commonly owned U.S. Pat. No. 6,162,169 which is hereby incorporated by reference herein. In such an embodiment, the transducer arrangement comprises a housing which can be fixed at the implantation site with reference to the skull, with a mechanically stiff coupling element which can move relative to the housing. In the housing there is an electromechanical transducer which to vibrates the coupling element.

The above signal processing components are controlled by a microcontroller included, for example, in speech processor 116. The microcontroller includes a storage area in which patient-specific audiologic adaptation parameters and the audiometry parameters of the above-noted signal generator are stored. The microcontroller and associated data storage may be implantable, such as within stimulator unit 126. In such embodiments, the programmable data are sent to the microcontroller via telemetry unit 102.

As noted, there may be a substantial number of parameters which may be customized to optimally fit a cochlear implant system to an individual patient. As will be described below, the values for a selected subset of these parameters may be obtained using a genetic algorithm. The selected subset of parameters and their respective values is collectively and generally referred to herein as a "parameter map," a "cochlear map" or "MAP." A "MAP" is also sometimes referred to as a "program."

In an embodiment, a MAP may be used to specify the speech strategy implemented in the cochlear implant system as well as parameters for implementation of the speech strategy. For example, within any given speech strategy, a large number of parameters may be specified to tailor the encoding and stimulation for an individual patient. Examples of parameters that may be specified by the MAP include but are not limited to the number of channels of stimulation to be presented to the patient, the configuration and number of intra-cochlear and/or extracochlear electrodes which are to be associated with each channel, the pulse repetition rate for each channel, the pulse pattern, the width of each pulse or between pulses, the number of spectral maxima to be presented, the mapping of sound pressure to stimulus current for each channel (threshold levels, comfort levels and compression curves), the frequency boundaries allocated for each channel, the front end filtering of the audio from the microphone (pre-emphasis), the automatic gain control threshold, channel-specific compression ratios, and attack and release times, etc.

In cochlear implant systems such as system 100 described above which provide electrical and mechanical stimulation (referred to as mixed-mode stimulation), additional parameters may be selected to tailor the cochlear implant system to an individual patient. Such parameters include, but are not limited to, loudness parameters such as long term loudness balance (that is, electrical and mechanical gains), short term gain manipulation parameters, particularly parameter(s) for signal-dependent gain adjustments. Such gain adjustment parameters may include, for example, parameters for adjustments to minimize cross-modal masking, and adjustments to emphasize speech features such as noise, frication or voicing.

Additional parameters may include frequency domain parameters. Such parameters may include, for example, parameters specifying the overall frequency boundaries allocated to electrical and mechanical stimulation channels, parameters specifying the slopes of filtering at the boundaries of each stimulation channel, parameters allocating frequency subbands (both quantity and boundaries) in each domain, parameters for filtering of the mechanical signal within the passband, for example, to match the hearing loss or for other purposes, etc.

Additional parameters may also include time domain parameters. Such parameters may include, for example, parameters for adjusting the electrical periodicity of pulse timing to be synchronized with the mechanical signal fluctuations, adjusting delays in the electrical stimulus to compensate for missing propagation delays of various middle ear and inner ear pathways, etc.

Additional parameters may also include binaural parameters. Such parameters may include, for example, parameters for adjusting stimulus timing to preserve interaural timing cures, adjustment of stimulus timing to suppress echo, improve localization, or improve sound source segregation, etc.

As used herein, the term 'parameter values' generally and collectively refers to values of parameters, whether selectable options are programmed on or off, and in general to any choices that are made during a fitting procedure.

Figure 2:
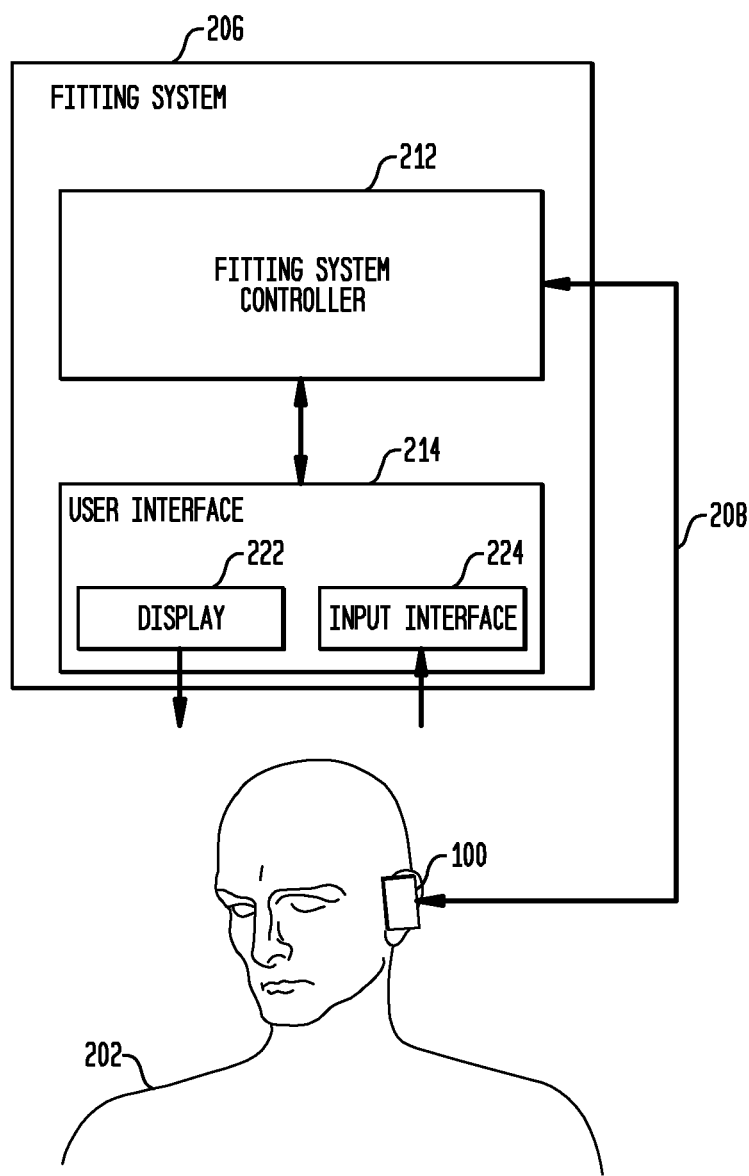
FIG. 2 is a schematic diagram illustrating one exemplary arrangement in which a recipient operated fitting system may be used in fitting a stimulating medical device, in accordance with an embodiment.

FIG. 2 is a schematic diagram illustrating one exemplary arrangement 200 in which a patient 202 operated fitting system 206 may be used in fitting a stimulating medical device, such as a cochlear implant 100, in accordance with an embodiment. In the embodiment illustrated in FIG. 2, sound processing unit 126 of cochlear implant 100 may be connected directly to fitting system 206 to establish a data communication link 208 between the sound processing unit 126 and fitting system 206. Fitting system 206 is thereafter bi-directionally coupled by means of data communication link 208 with sound processing unit 126. It should be appreciated that although sound processing unit 126 and fitting system 206 are connected via a cable in FIG. 2, any communications link now or later developed may be utilized to communicably couple the implant and fitting system.

Fitting system 206 may comprise a fitting system controller 212 as well as a user interface 214. Controller 212 may be any type of device capable of executing instructions such as, for example, a general or special purpose computer, digital electronic circuitry, integrated circuitry, specially designed ASICs (application specific integrated circuits), firmware, software, and/or combinations thereof. User interface 214 may comprise a display 222 and an input interface 224. Display 222 may be, for example, any type of display device, such as, for example, those commonly used with computer systems. Input interface 224 may be any type of interface capable of receiving information from a recipient, such as, for example, a computer keyboard, mouse, voice-responsive software, touch-screen (e.g., integrated with display 222), retinal control, joystick, and any other data entry or data presentation formats now or later developed.

Figure 3:
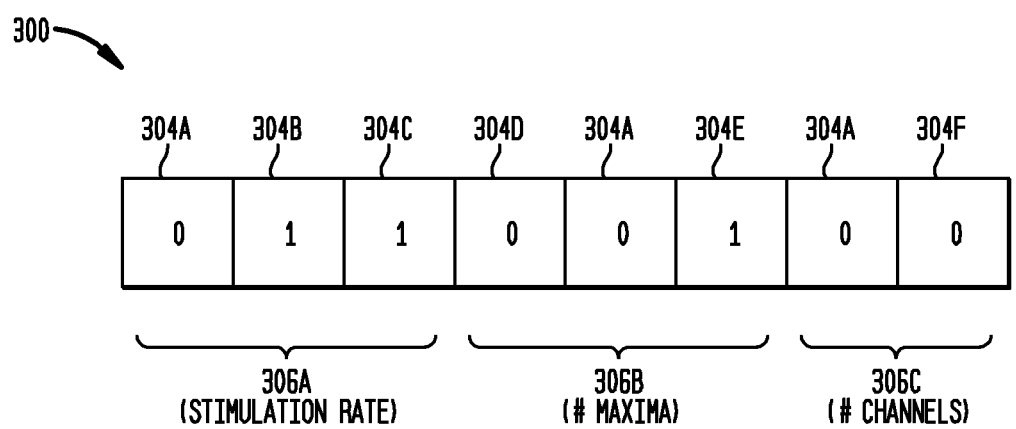
FIG. 3 illustrates an exemplary MAP comprising a set of 8 binary genes, in accordance with an embodiment.

Fitting system 206 may be configured to perform a MAP search using a genetic algorithm. In performing the genetic algorithm search, fitting system 206 may represent the MAPs using a bit string comprising a set of $N_b$ 'genes' (bits), wherein the number of possible unique MAPs is $2^{Nb}$. FIG. 3 illustrates an exemplary MAP 300 comprising a set of 8 binary genes 304A-304H ($N_b$=8). Each of the 8 bits 304 may be used to individually or collectively designate several parameters for cochlear implant system 100.

In the example shown in FIG. 3, three such parameters 306A-306C are designated. Three bits 304A-304C are used to select a parameter 306A of stimulus rate (the rate, in Hz, at which high-energy channels are selected and stimulus pulses are delivered to groups of N electrodes), three bits 304D-304F are used to select a parameter 306B of spectral maxima counts (the number N of electrodes periodically selected to be stimulated, representing the N frequency bands with the highest energy at the time), and the remaining two bits 304G-304H select a parameter 306C of the quantity of channels or frequency bands, used to represent the sound spectrum. Other parameters are assumed to be constant or derived from one of the three represented parameters 306.

It should be understood that FIG. 3 is exemplary only and provided to illustrate how a bit string may be used to represent various parameters of a MAP; and, in other embodiments the number of bits and what they represent may be different in alternative embodiments. A further description of an exemplary mechanisms for representing MAPs using bits strings is provided in U.S. patent application Ser. No. 10/963,594 entitled "Using a Genetic Algorithm to Fit a Cochlear Implant System to a Patient,", the entire contents of which are hereby incorporated by reference.

Figure 4:
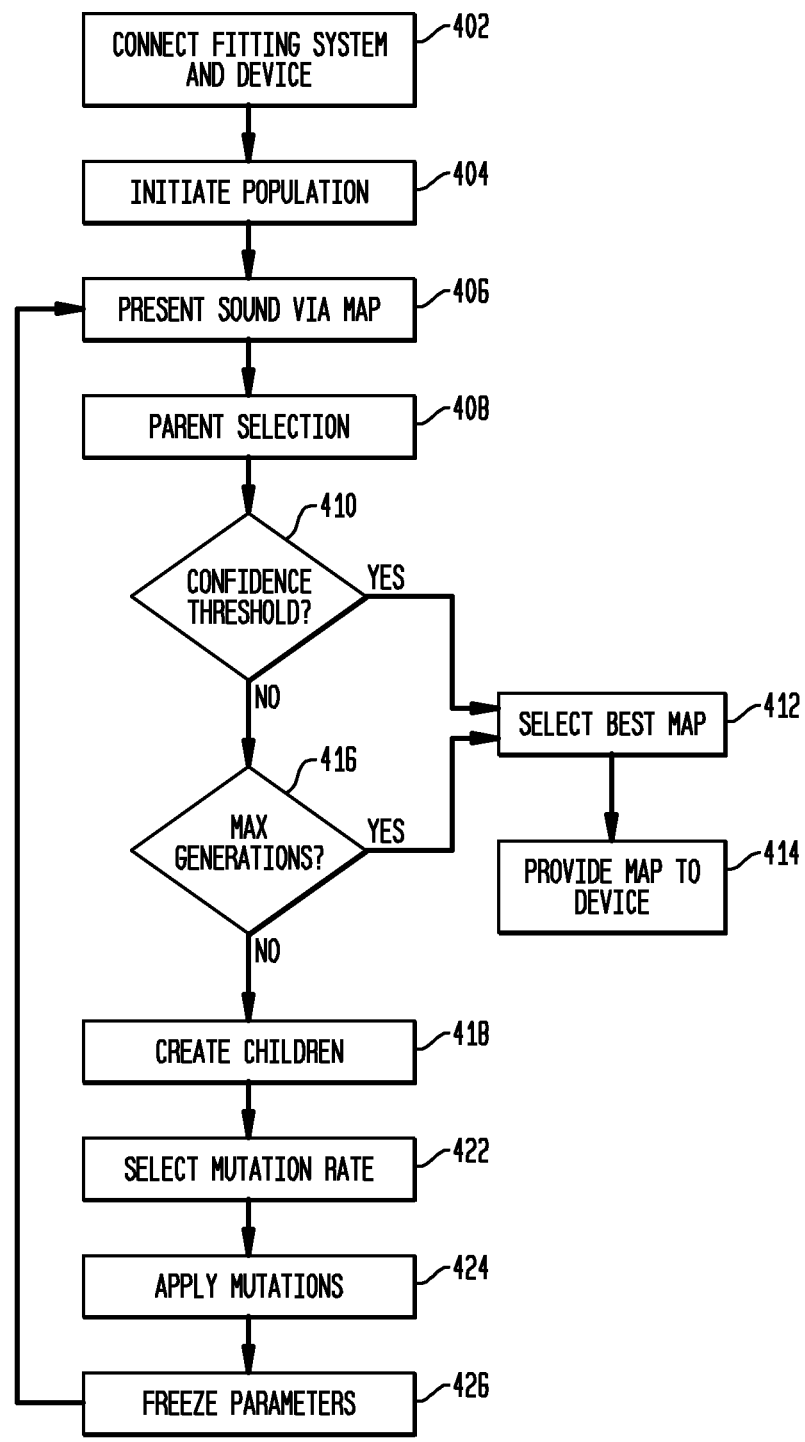
FIG. 4 is a high-level flow chart of an exemplary method for determining a MAP using a genetic algorithm, in accordance with an embodiment.

FIG. 4 is a high-level flow chart of an exemplary method for determining a MAP using a genetic algorithm, in accordance with an embodiment. FIG. 4 will be discussed with reference to the fitting system illustrated in FIG. 2.

A patient 202 may initiate the process by connecting cochlear implant 100 to fitting system 206 at block 402. This may be accomplished by plugging a cable into the speech processor 126 of the cochlear implant 100 and the fitting system 206. Or, for example, fitting system 206 and cochlear implant 100 may connect wirelessly in response to, for example, the recipient entering an instruction via user interface 214 that instructs fitting system 206 to wirelessly initiate a connection with cochlear implant 100. This connection may also cause the fitting system to begin some initialization procedures. These initialization procedures may include a calibration step to help ensure that if the fitting system 206 delivers a sound signal to the patient 202 via a speaker at a specified loudness, the sound is delivered with a constant sound level pressure to the sound processing unit 126 of the cochlear implant 100 by the fitting system 206.

The fitting system 206 may generate an initial population of MAPs at block 404. In an embodiment, the initial population may comprise 8 selected MAPs. It should be noted that this number need not be 8, but may vary depending on the implementation. Various techniques may be used to select this initial generation of MAPs. For example, this selection may be performed by selecting at random from among the set of possible MAPs. Or, for example, in order to insure greater diversity among the selected initial generation of MAPs, the MAPs may be selected so that the each parameter value is represented in at least one MAP. For parameters in which the number of possible variables is greater than the number of MAPs in the initial generation, the values may be randomly selected such that each MAP in the initial generation has a unique value for the parameter. For example, if there are 12 possible parameter values, a first one of the parameter values may be randomly selected from among the 12 possible values, and then when selecting the parameter value for the second MAP the fitting system selects from amongst the 11 remaining unselected values, and so on.

Or, for example, in an embodiment, in order to insure that this initial MAP set has a sufficient measure of heterogeneity, the MAPs diversity may computed. In one embodiment, diversity is defined as the average Hamming distance between the various MAPs, and it ranges between 0 and 1, with 1 indicating maximum diversity and 0 indicating minimum diversity. If the diversity is below a threshold, for example, 0.53, then the initial generation has an insufficient diversity, and the fitting system 206 may select a new set of MAPs. Moreover, pre-selected MAPs may also be included among the MAPs of the first generation. These pre-selected MAPs may be drawn, for example, from prior runs of the fitting procedure, MAPs stored in a memory of fitting system 206, or MAPs selected by a clinician based on his experience, suggestions and recommendations from others, etc. This initial population of MAPs may be referred to as the first generation of MAPs.

At block 406, audible signals processed by the population of MAPs are presented to the patient. This may involve fitting system 206 sequentially providing each MAP to the patient's cochlear implant 100 and then presenting an audible signal that that is processed by the provided MAP. The audible signal may be a sound token that comprises any type of sound, such as a single speaker reading aloud from a newspaper or a passage from an audio book, a particular piece of music, or portion of same, a musical instrument, a car horn, etc. The audible signals (e.g., sound tokens) may be stored in a file contained in a library of audible signals that is stored, for example, in fitting system 206 or in an external storage device connected to fitting system 206.

In an embodiment, fitting system 206 may randomly select a sound token for each of the 8 MAPs. Fitting system 206 may then download the MAP corresponding to a particular sound token to the cochlear implant 10, then play the sound token. This sound token may be played using, for example, one or more speakers connected to fitting system 206, such as, for example, a set of headphones worn by the patient 202. Further, patient 202 and fitting system 202 may be located in a room such as, for example, a sound proof room, designed to minimize external noise from interfering with the presentation of the audible signal. Or, for example, fitting system 206 may provide the audible signal directly to cochlear implant 100 via data communications link 208. Cochlear implant 100 may then receive the played sound token, process the received sound using the downloaded MAP, and present the resulting stimulation to the patient. Presenting stimulation to a patient corresponding to a sound token processed by a particular MAP is referred to herein as presenting the MAP and sound token to the patient.

After fitting system 206 presents the first sound token to the patient 202, the fitting system 206 may download the next MAP to the cochlear implant 100 and then play the corresponding sound token to the patient 202. This process may then continue sequentially until fitting system 206 presents all 8 MAPs to the patient 202.

After fitting system 206 presents each of the sound tokens and corresponding MAPs to the patient 202, the patient 202 may select the 4 MAPs that the patient considered to be the best MAPs at block 408. Fitting system 206 may then receive this selection from the patient 202 and these 4 best MAPs are selected as the parent MAPs for generating the next generation of MAPs. Fitting system 206 may use user interface 214 to obtain the patient's MAP selections. For example, fitting system 206 may present a graphical user interface (GUI) on display 222 that provides icons or checkboxes that a user may select using input interface 224 to make their selections.

In another embodiment, the patient 202 may simply identify which sound tokens were perceived as good by the patient 202 using, for example, user interface 214. Using this indication, fitting system 206 may select the parents for the next generation of MAPs. For example, if the patient 202 identifies more than 4 presented MAPs as good, fitting system 206 may randomly select 4 MAPs from the MAPs identified as good. Or, if the patient identifies less than 4 MAPs as good, fitting system 206 may select the MAPs identified as good as parent MAPs and then randomly select from amongst the MAPs not yet visited to select additional parent MAPs to obtain a total of 4 parent MAPs.

It should be noted that these are but some exemplary mechanisms that may be used at blocks 406 and 408 for selecting parent MAPs from the population of MAPs, and other mechanisms may be used without departing from the present invention. For example, mechanisms for selecting parent MAPs may be used such as described in U.S. patent application Ser. No. 12/557,208, entitled "Using a Genetic Algorithm to Fit a Medical Implant System to a Patient,", by Lineaweaver et al. filed on Sep. 10, 2009, the entire contents of which are hereby incorporated by reference. Further, it should be noted that although blocks 406 and 408 are illustrated as separate blocks, this was done for illustrated purposes, and in embodiments they may be combined or involve an iterative process where the two blocks are repeated until a certain condition occurs, such as a particular number of MAPs are selected.

Fitting system 206 may then check to see if a confidence threshold has been reached at block 410 for the selected MAPs. In an embodiment, fitting system 206 may determine that the confidence threshold has been reached if the value of each bit of the MAP bit string is considered to have converged and its value is known with a particular confidence level based on the historical distribution of that bit. For instance, bit #1 may be considered converged if it has historically either been a "1" or a "0" a particular percentage of the time (e.g., 95% of the time) over its entire history. As such, probability dictates that there is a 95% chance that this bit will be the same value again in a subsequent generation.

When all bits reach the specified confidence level (e.g., 95%), fitting system 206 may determine that the confidence threshold has been met. In other words, in this example, the fitting system 206 determines that the confidence threshold has been met if the confidence level for each of the bits exceeds the specified confidence level (e.g., 95%). Further, in an embodiment, fitting system 206 may implement an expedited convergence algorithm such as discussed in U.S. patent application Ser. No. 12/557,233, entitled "USING A GENETIC ALGORITHM EMPLOYING AN EXPEDITED CONVERGENCE MECHANISM IN FITTING A MEDICAL IMPLANT SYSTEM TO A PATIENT," by Lineaweaver et al. filed on Sep. 10, 2009, the entire contents of which are hereby incorporated by reference.

If at block 410 the confidence threshold has not been achieved, fitting system 206 may determine if the maximum number of generations has been reached at block 416. If so, fitting system 206 may proceed to block 410 to select the final MAP. Otherwise the algorithm continues to block 418.

Fitting system 206 may determine if the maximum number of generations has been reached by maintaining a tally of each pass through block 416 and then comparing this tally against a predetermined value specifying the maximum number of generations to be used in determining the final MAP. For example, in an embodiment, fitting system 206 may set a generation number variable, G, equal to one (G=1) at block 404, and then increase G by 1 (G=G+1) at block 418. It should be noted that this is but one mechanism in which fitting system 206 may maintain a generation number variable G that is equal to the current generation number of the genetic algorithm search, and other mechanisms may be employed.

Fitting system may then generate child MAPs at block 418. Various techniques may be used for generating the child MAPs. For example, in an embodiment, a child MAP may be generated by pairing two of the parent MAPs selected at block, selecting a cut point, and then generating two children MAPs from the selected parents. In an embodiment, the genes for a child MAP to the left of the cut point may come from one parent, and the genes to the right of the cut point may come from the other parent.

Figure 5:
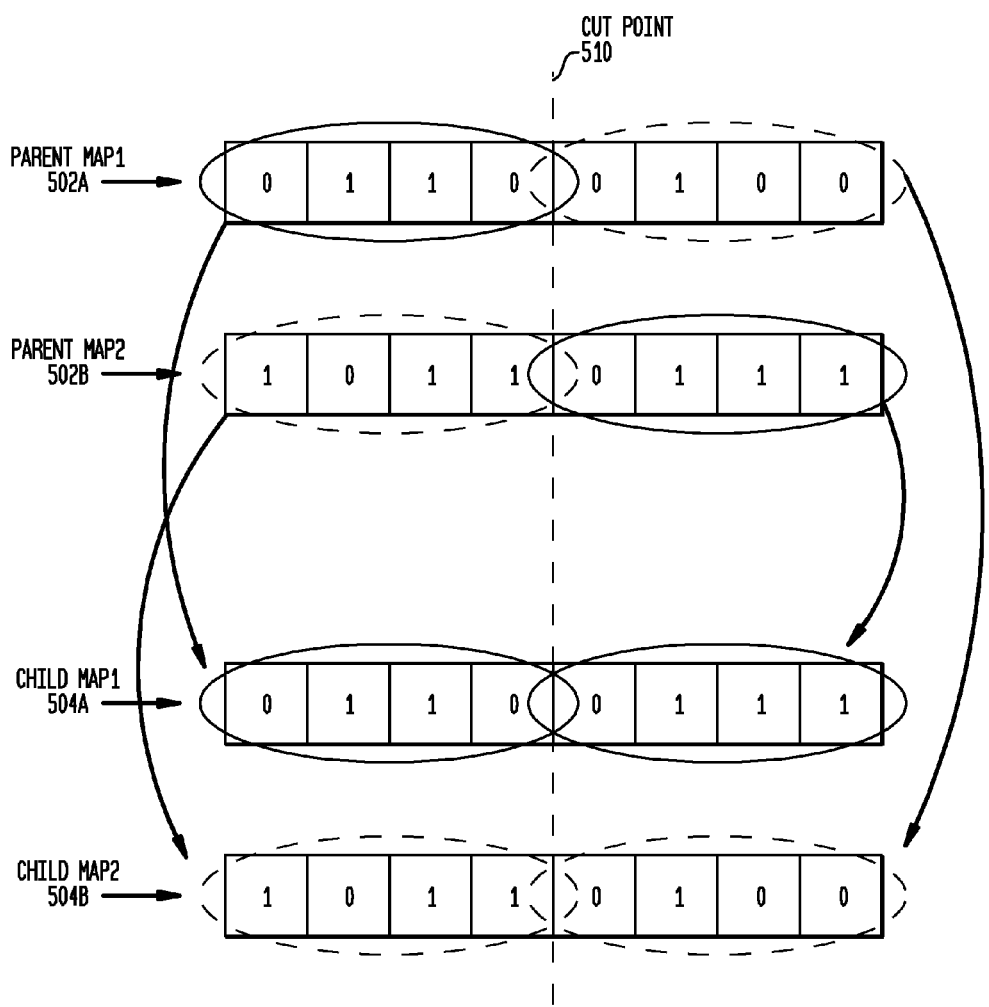
FIG. 5 illustrates one example of how an offspring MAP may inherit genes from each parent MAP, in accordance with an embodiment

FIG. 5 illustrates one example of how an offspring MAP may inherit genes from each parent MAP, in accordance with an embodiment. In the illustrated example, each parent MAP 502A and 502B is represented by an 8 bit string. Fitting system 206 may select a cut point 510 for the bit string of each parent MAP 502A and 502B. The selected cut point 510 may be between any particular bits of the bit strings, and in FIG. 5 the cut point 510 is selected in the middle of each bit string. Further, in the illustrative example, the cut point is allowed to vary randomly across pairings. For example, in an embodiment, the fitting system 206 may analyze the two parent MAPs to identify bits that are different between the parents, and then randomly select a cut point between the bits identified to be different. Alternatively, the cut points can be made in the same position for all the pairings.

Then, fitting system 206 may generate two child MAPs 504A and 504B from the parent MAPs 502, where the first child MAP 504A includes bits of parent MAP 502A to the left of the cut point 510 (i.e., the first 4 bits) and the of the parent MAP 502B to the right of the cut point 510 (i.e., the last 4 bits). Similarly, the genes of the second child MAP 504B include the first 4 bits of parent MAP 502B and the last 4 bits of parent MAP 502A. It should be noted that this is but one example of how child MAPs may be generated from parent MAPs, and other mechanisms may be used, and other techniques may be used in generating child MAPs, such as those such as those discussed in the above referenced U.S. patent application Ser. No. 12/557,233, entitled "Using a Genetic Algorithm to Fit a Medical Implant System to a Patient,". Further, if in an embodiment, more MAPs are generated at block 418 than are to be presented to the patient at block 406 (e.g., more than 8 child MAPs are generated), block 418 may also include selecting from amongst the generated child MAPs, the next generation of MAPs to be presented to the patient. Various techniques may be used for selecting the new generation of MAPs, such as those discussed in the above-referenced U.S. patent application Ser. No. 12/557,208, entitled "Using a Genetic Algorithm to Fit a Medical Implant System to a Patient,".

Figure 6A:
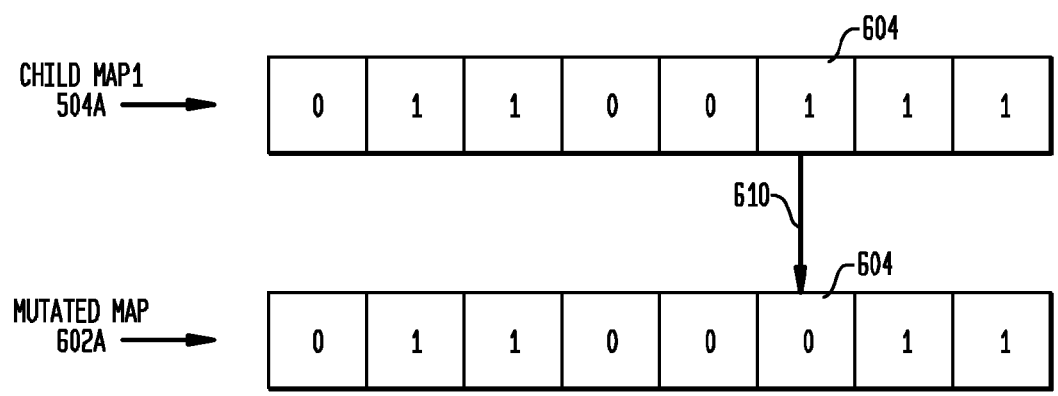
FIG. 6A illustrates a MAP undergoing a single bit mutation, in accordance with an embodiment
Figure 6B:
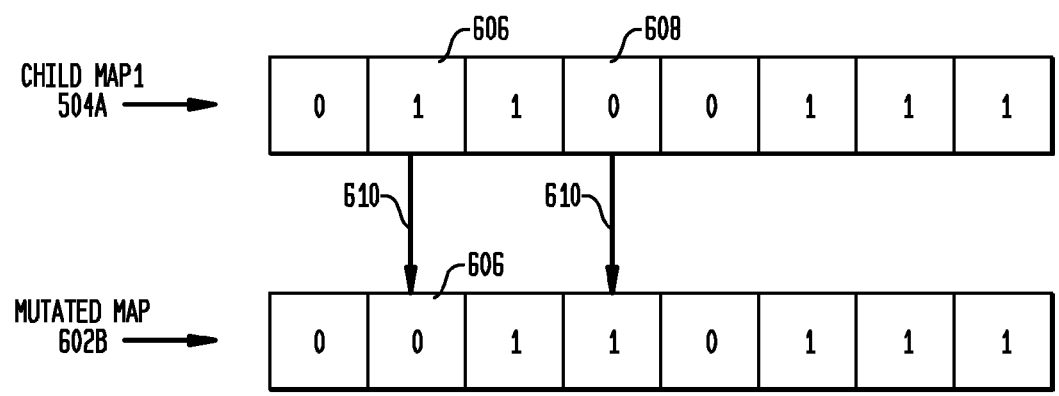
FIG. 6B illustrates a MAP undergoing a two bit mutation, in accordance with an embodiment.

Referring back to FIG. 4, fitting system 206 may select a mutation rate at block 422. In an embodiment, a mutation refers to inverting a bit or bits of a MAP; and, the mutation rate refers to the probability that a bit is inverted. FIGS. 6A and 6B illustrate an exemplary MAP represented by a bit string for use in explaining mutations, in accordance with an embodiment. For explanatory purposes, FIGS. 6A and 6B illustrate the child MAP 504A discussed above with reference to FIG. 5. FIG. 6A illustrates child MAP 504A undergoing a single bit mutation to provide Mutated MAP 602A, in accordance with an embodiment. In this example, the mutation rate is assumed to be 1/8. That is, the probability that a bit undergoes a mutation is 1/8. As illustrated, a bit 604 of child MAP 504A is initially a "1" and then undergoes a mutation 612 that inverts bit 604 from a "1" to a "0."

FIG. 6B illustrates child MAP 504A undergoing a two bit mutation to provide Mutated MAP 602B, in accordance with an embodiment. As illustrated, 2 bits 606 and 608 are selected and mutated 610 to invert the value of the stored bit 606 and 608. Particularly, bit 606 is mutated 610 to invert the value from a "1" to a "0." And, bit 608 is mutated 610 to invert the bit 608 from a "0" to a "1." Although in this example, the mutation rate is 1/8, the probability that a bit is mutated may be applied individually to each bit, and thus the number of bits mutated in an individual 8 bit MAP may be more, less, or equal to 1. It should be noted, that the examples of FIGS. 6A and 6B are provided to illustrate the concept of mutations and as such are simplified and use high mutation rates for illustrative purposes. In actual implementation, the mutation rate may be such that only a fraction of bits from the entire set of child MAPs selected at block 418 are mutated. For example, in one embodiment, the mutation rate may vary between 3% and 6%. Thus, in implementation only a small number of child MAPs selected at block 418 may be mutated.

As demonstrated in FIGS. 6A and 6B, mutations have the ability to alter the child MAPs selected at block 418 to different MAPs. Thus, a higher mutation rate increases the likelihood that a MAP will be mutated and thus move the genetic algorithm search into MAP regions not yet visited by the genetic algorithm.

In an embodiment, the mutation rate selected at block 422 may be dynamic and vary based on certain factors. For example, in one embodiment, the mutation rate may initially be selected as a default value (e.g., 3%), and then vary (e.g., between 3 and 6.5%) based on the homogeneity of the child MAPs generated at block 418. As used herein the term "homogeneity" refers to the similarity of the MAPs. For example, a set of child MAPs is considered more homogenous if multiple MAPs in the set are identical, or if the MAPs in the set are likely to create the same child MAPs, etc. In one such embodiment, fitting system 206 may adjust the mutation rate based on the number of identical (i.e., matching) MAPs selected at block 422. For example, if no MAPs are identical to any other MAP, fitting system 206 may select a 3% mutation rate. If two MAPs are identical, fitting system 206 may select a 4% mutation rate. If any 3 MAPs are identical, fitting system may select a 4.5% mutation rate. If 4MAPs match at least one other MAP (e.g., there are 4 identical MAPs, or there are 2 sets of 2 identical MAPs), fitting system 206 may set the mutation rate to 5%. If 5 MAPs match at least one other MAP (e.g., there are 5 identical MAPs, or there are 1 sets of 2 identical MAPs and 1 set of 3 identical MAPs), fitting system 206 may select a mutation rate of 5.5%. If 6 MAPs match at least one other MAP (e.g., there are 6 identical MAPs, there are 3 sets of 2 identical MAPs, there are 2 sets of 3 identical MAPs, etc.), fitting system 206 may select a mutation rate of 6%. If 7 MAPs match at least one other MAP, fitting system 206 may select a mutation rate of 6%. And, if 8 MAPs match at least one other MAP, fitting system 206 may select a mutation rate of 6.5%. It should be noted that this is but one example of a method in which a fitting system 206 may use the homogeneity of the selected child MAPs in setting the mutation rate, and other mechanisms may be used. For example, the mutation rates may vary between a different minimum and maximum, the change(s) in rates from one possible number of matching MAPs to another may be different, etc.

In another embodiment, rather than basing the mutation rate on the number of matching MAPs, fitting system 206 may select the mutation rate based on an analysis of the MAPs selected for presentation to the patient. For example, at block 422, fitting system 206 may determine if the MAPs being generated at block 418 do not venture beyond a limited number of MAPs. If none of these MAPs meet the fitness criterion (e.g., the patient may indicate at block 414 that the final MAP is not acceptable), this may indicate that the algorithm is trapped in a local optimum. If fitting system 206 determines that the MAPs do not venture beyond a limited region (e.g., the search is trapped in a local optimum), fitting system 206 may select a higher mutation rate than if the fitting system 206 determines that the genetic algorithm is not so constrained.

In another example, fitting system 206 may adjust the mutation rate based on a statistical analysis of the MAPs. In one such example, fitting system 206 may perform a statistical analysis of the MAPs using a Markov Matrix that, given a particular mutation rate, provides the likelihood of any MAP mutating to any other MAP. For example, in an embodiment, the likelihood of a particular MAP being mutated to another MAP in which only a single mutation (i.e., inverting a single bit) is required would be higher than the likelihood of the particular MAP mutating to another MAP that would require multiple mutations. These likelihoods may be stored in a Markov Matrix.

Fitting system 206 may also compute the likelihood of the selected MAPs (i.e., the MAPs created at block 418) generating each possible MAP (i.e., being created as a child MAP at block 418 in the next pass thru blocks 406-426), assuming an equal likelihood of the patient selecting each MAP, an equal likelihood of each MAP being selected to pair with any of the other presented MAPs (i.e., MAPs used to process the audible signals presented to patient 202 at block 406), and an equal likelihood of any particular cut-point being selected when generating child MAPs. This computed likelihood of each MAP being generated in the next pass (i.e., created as a child MAP at block 418 during the next pass) from the selected MAP (i.e., the MAPs created at block 418 during the current pass) may be combined with the computed Markov Matrix to provide a likelihood of each MAP being created and selected for presentation to the patient. Fitting system 206 may then examine these calculated likelihoods, and if the likelihood of generating any MAP falls below a threshold, fitting system 206 may increase the mutation rate. In another embodiment, rather than increasing the mutation rate if only one MAP falls below the threshold, fitting system 206 may instead only increase the mutation rate if a particular number of MAPs (e.g., 2 MAPs, 4 MAPs, 40 MAPs, etc.) fall below the threshold. It should be noted that these are but some examples of how fitting system 206 might perform a statistical analysis in selecting the mutation rate, and other mechanisms may be used without departing from the present invention.

After selecting the mutation rate at block 422, fitting system 206 may mutate the child MAPs at block 424. In an embodiment, fitting system 206 may apply the mutation rate to each bit of the child MAPs to determine whether to mutate (e.g., invert) the bit. For example, fitting system 206 may generate a random number between 1 and 100 for each bit, and if the randomly generated number is less than or equal to the selected mutation rate, then fitting system 206 may mutate (e.g., invert) the bit. It should be noted that this is but one simple example provided to illustrate how fitting system 206 may use a mutation rate to mutate MAPs, and other mechanisms may be used without departing from the invention.

At block 426, fitting system 206 may determine whether to freeze any particular bits or groups of bits for the MAPs. Although in this example freezing occurs after mutation, it should be understood that freezing may occur at other times in the process, such as for example, prior to mutating the bits. For example, fitting system 206 may determine whether to freeze any bits when checking whether the confidence threshold is exceeded at block 410.

As noted above with reference to FIG. 3, a parameter (e.g., stimulation rate 306A, # Maxima 306B, # Channels 306C, etc.) may be specified by a group of bits in each MAP. In an embodiment, fitting system 206 may determine to freeze the bits for a particular parameter if the likelihood of convergence for the parameter exceeds a particular threshold. As used herein the term likelihood of convergence refers to the likelihood that a particular parameter or portion of the parameter has converged on a particular value. In an embodiment, the likelihood of convergence is considered to have exceeded the threshold if each bit of the parameter is known with a confidence level exceeding a particular threshold (e.g., 95%). For example, fitting system 206 may determine that a parameter has converged if the value of each bit for the parameter is known with a particular confidence level based on the historical distribution of each bit. For instance, bit #1 may be considered converged if it has historically either been a "1" or a "0" a particular percentage of the time (e.g., 95% of the time) over its entire history. As such, probability dictates that there is a 95% chance that this bit will be the same value again in a subsequent generation. When all bits for the parameter reach this confidence level (e.g., 95%), fitting system 206 may determine that the parameter has converged.

If fitting system 206 determines that a particular parameter has converged, fitting system 206 may freeze the parameter. Once a parameter is frozen, fitting system 206 will maintain this parameter as fixed through the remaining generations of the genetic algorithm. Thus, regardless of the selected cutpoint or mutation determination, the values for the bits of a frozen parameter will not change. Further, fitting system 206 will not mutate bits for frozen parameters in an embodiment. As an example, if fitting system 206 determines that stimulation parameter 306A (FIG. 3) has converged, fitting system 306A may freeze the bit values for parameter 306A. Thus, in subsequent generations bits 304A, 304B, and 304C will remain equal to their frozen values.

In another embodiment, fitting system 206 may group multiple parameters together, and freeze the parameters only if fitting system 206 determines that all parameters in the group have converged. For example, in an embodiment, the stimulation rate and # of maxima parameters 306A and 306B may be grouped together, and only frozen if each bit of both parameters (i.e., bits 304A through 304E) is known with the specified confidence level. Then, the genetic algorithm may only vary bits of the other parameters in subsequent iterations of the genetic algorithm search. It should be noted that this is but one example illustrating how multiple parameters may be grouped for purposes of determining whether to freeze the values for the parameters and other groupings may be used in other embodiments. For example, in a MAP that comprises parameters such as the stimulation rate 306A, # Maxima 306B, and # channels, 306C along with other parameters, fitting system 206 may group parameters 306A, 306B, and 306C and only freeze the parameters when each bit of for each of these parameters is known with the specified confidence level.

In another embodiment, bit string MAPs may use a lookup table to map bit strings to parameters. In such an embodiment, there may not be a one to one correspondence between a bits location in the MAP and the parameter to which it corresponds. For example, in the embodiment illustrated in the above-discussed FIG. 3, the first three bits 304A-304C correspond to the stimulation rate. Thus, these three bits may be used to specify up to 8 different stimulation rates (2^3). If, however, in an implementation, there are only 6 possible stimulation rates, then 2 of the 8 possible combinations may be used in an embodiment in specifying another parameter. In such cases, a look up table may be stored and used by fitting system 206 to map bit string MAPs to their corresponding parameter values. Further, in such an embodiment, fitting system at block 426 may examine the MAPs and determine if any of the parameters specified by the MAPs correspond to frozen parameters. If fitting system 206 determines that any frozen parameters have been changed, fitting system 206 may revert these frozen parameters back to their frozen value prior to returning to block 406.

After freezing at block 426, fitting system 206 may return to block 406 and present the generated sound tokens processed by the next generation of MAPs to the patient. The process may then continue until either sufficient diversity is achieved at block 410 or the maximum number of generations is reached at block 414.

Once the confidence threshold or maximum number of generations has been reached, fitting system 206 may determine, at block 412, the particular MAP to be used by the cochlear implant 100, referred to herein as the final MAP. Various techniques may be used for determining the final MAP depending, for example, on how the process was terminated. For example, if the confidence threshold was reached by a determination that each bit of the MAP is known with a confidence level exceeding the specified confidence level (e.g., 95%), then fitting system 206 may simply use these known bit values for the final MAP. It should be noted that, although referred to as a final MAP herein, the final MAP may be changed after fitting, such as, for example, by the patient 202 re-fitting the cochlear implant 100 at a later time.

If block 406 is reached, however, due to the maximum number of generations being reached at block 416 or, for example, a determination that the confidence threshold was exceeded by some other mechanism, fitting system 206 may use various other mechanisms for determining the final MAP. For example, fitting system 206 may present sound tokens processed by each of the final selected MAPs to the patient 202 and receive an indication from the patient regarding which MAP is considered the best MAP. In another embodiment, the final MAP may be selected by fitting system 206 computing a Simpson Diversity Index (SDI) for each parameter in each generation to created SDI Matrix (#parameters X #generations), such as discussed in more detail in U.S. patent application Ser. No. 12/557,208, entitled "Using a Genetic Algorithm to Fit a Medical Implant System to a Patient,", by Lineaweaver et al.

After, the final MAP is determined at block 412, fitting system may download this final MAP to cochlear implant 100 for subsequent use at block 414. In addition, fitting system 206 may store this final MAP along with information identifying the patient 202 and/or cochlear implant 100 in a storage of fitting system 206. Thus, in the event the patient's cochlear implant 100 becomes corrupted; fitting system 100 may be able to more quickly re-provide the determined MAP to cochlear implant 100. Or, for example, if the genetic algorithm search is repeated for the patient at a later date, an audiologist may be able to view and compare the newly determined MAPs as well as previously determined MAPs for the patient, or even use the previously determined MAP(s) as one of the MAP in the initial generation of the genetic algorithm search.

Further, fitting system 206 may present, at block 414, a user interface to the patient 202 that includes an icon for allowing the patient 202 to identify whether the patient considers the final MAP determined at block 412 to be acceptable or not, in an embodiment. If not, the process may return to block 418, and the previously selected MAPs used to generated new children. If, so, the process may end.

In yet another embodiment, the genetic algorithm may use two or more populations, rather than a single larger population. A population refers to a subset of parameters that may be selected for a MAP during a genetic algorithm search. For example, the genetic algorithm process may be performed two or more times with a different set of MAP parameters for each genetic algorithm search. In other words, a genetic algorithm search may be performed for each population. In one such example, in the first genetic algorithm search, the parameters represented by the MAP (i.e., the first population) may be more critical parameters. Then in the second genetic algorithm search, the parameters determined in the first search will be fixed and the second genetic algorithm search used to identify less critical parameters (i.e., the second population). For example, in an embodiment, a first genetic algorithm search may be performed using MAPs that specify the stimulation rate, number of electrodes, and number of Maxima to be used (collectively referred to as the first population). Other parameters may be set to default values during this first search. Then, the parameter values determined during this first genetic algorithm search are fixed, and the second genetic algorithm search may be performed using these previously determined values as fixed terms. The MAP parameters (i.e., the second population) used in the second genetic algorithm may include parameters, such as values for the type of and shape of filters, etc. In other words, the fitting system 206 may sequentially perform multiple genetic algorithm searches where values for different subsets of parameters are identified in each search, and the values identified in previously performed searches are used as fixed values in subsequent genetic algorithm searches.

The above discussed processes, such as FIG. 4, and mechanisms may be embodied on software executable by a computer. Additionally, in an embodiment fitting system 206 may be a patient's home computer, personal digital assistant (PDA) or other device on which such software is loaded. Additionally, in such an embodiment, a piece of hardware may be used for allowing the patient's computer to communicate with the patient's cochlear implant for the purposes of, for example, changing the MAP used by the patient's cochlear implant. This hardware may be connected to the patient's computer, PDA, etc. using for example, as USB interface, a firewire interface or any other suitable mechanism. Or, for example, the patient's computer, PDA, etc. may communicate wirelessly with the patient's cochlear implant using Wi-Fi, Bluetooth, or any other suitable wireless interface included in the computer and cochlear implant. Additionally, in embodiments, the patient could perform optimizations at using signals of his or her own choosing (e.g., a spouse's voice, a musical piece, etc.) or simply using the microphone input of the stimulating medical device. In such embodiment, the software may provide the patient with the ability to upload and store these audible signals for use by the genetic algorithm.

It should be noted that although the above-discussed embodiments were discussed with reference to a cochlear implant, in other embodiments a fitting system may be used to permit a recipient to measure the dynamic range of other stimulating medical devices, such as, for example, bone conduction devices, auditory brain stimulators, etc.

Various implementations of the subject matter described, such as the embodiment of FIG. 2, components of may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for at least partially fitting a medical implant system to a patient comprising:

executing a genetic algorithm to select a determined value set comprising values for a plurality of fitting parameters, the genetic algorithm comprising:
presenting signals processed according to a plurality of initial value sets to the patient using the medical implant system;
receiving patient feedback in response to the presented signals processed according to the initial value sets;
selecting, based on the patient feedback, one or more of the initial value sets;
generating a successor generation of one or more value sets using said selected one or more initial value sets;
selecting a mutation rate based on at least one of the one or more successor value sets, wherein the selecting a mutation rate comprises:
choosing the mutation rate based on a homogeneity of the successor value sets, wherein the choosing the mutation rate comprises:
determining the number of successor value sets that match at least one other successor value set; and
determining the mutation rate based on the determined number of matching value sets;
mutating at least a portion of at least one of the one or more successor value sets using the selected mutation rate to form one or more mutated value sets; and
selecting the determined value set from the one or more mutated value sets; and providing said determined value set to said medical implant system for use in providing stimulation to the patient.

2. The method of claim 1, wherein each value of the value set is represented by a plurality of bits; and wherein the mutating comprises:
inverting at least one bit of at least one value set.

3. The method of claim 1, wherein executing a genetic algorithm further comprises:
computing a likelihood of convergence for at least one given value of a given one of the selected one or more initial value sets; and
freezing the at least one given value based on whether the computed likelihood exceeds a particular confidence level.

4. The method of claim 3, wherein computing a likelihood of convergence for at least one value of the value set comprises:
computing a likelihood of convergence for each value for at least one parameter of the value set; and
wherein freezing the value comprises:
freezing each value for the at least one parameter if each value for the parameter exceeds the particular confidence level.

5. The method of claim 4, wherein each value of the value set is represented by a plurality of bits, and wherein computing a likelihood of convergence for each value comprises:
computing the percentage of time a bit has a particular value using values of the bit in previous generations of the genetic algorithm.

6. The method of claim 1, wherein presenting signals processed according to the plurality of initial value sets comprises:
providing an initial value set to the medical implant system; and
providing a signal to the patient that is processed by the medical implant system using the provided initial value set.

7. The method of claim 6, wherein:
the signal provided to the patient is a first signal;
the providing signals processed according to the plurality of value sets further comprises:
providing a second signal to the patient system that is processed by the medical implant system using the provided value set; and
the receiving patient feedback comprises:
receiving patient feedback regarding the provided first signal processed using the provided value set; and
receiving patient feedback regarding the provided second signal processed using the provided value set.

8. The method of claim 1, wherein the medical implant system is a cochlear implant system and wherein the signals are audible signals.

9. A system for at least partially fitting a medical implant system to a patient comprising:
a processor configured to execute a genetic algorithm to select a determined value set comprising values for a plurality of fitting parameters, wherein the processor in executing the genetic algorithm is configured to:
present signals processed according to a plurality of initial value sets to the patient using the medical implant system,
receive patient feedback in response to the presented signals processed by the initial value sets,
select, based on the patient feedback, one or more of the initial value sets,
generate a successor generation of one or more value sets using said selected one or more initial value sets,
select a mutation rate based on at least one of the one or more successor value sets, wherein in selecting a mutation rate the processor is further configured to choose the mutation rate based on a homogeneity of the successor value sets, wherein in choosing the mutation rate the processor is further configured to:
determine the number of successor value sets that match at least one other successor value set; and
determine the mutation rate based on the determined number of matching value sets, and
mutate at least a portion of at least one of the one or more successor value sets using the selected mutation rate to form one or more mutated value sets; and
an interface configured to provide at least one of the value sets to the medical implant system for use by the medical implant system in providing stimulation to the patient.

10. The system of claim 9, where the processor is further configured to represent each value of the value set by a plurality of bits, and wherein the processor in mutating is further configured to invert at least one bit of at least one value set.

11. The system of claim 9, wherein the processor in executing a genetic algorithm is further configured to:
compute a likelihood of convergence for at least one given value of a given one of the selected one or more initial value sets, and
freeze the at least one given value based on whether the computed likelihood exceeds a particular confidence level.

12. The system of claim 11, wherein:
the processor in computing a likelihood of convergence for at least one value of the value set is further configured to compute a likelihood of convergence for each value for at least one parameter of the value set; and
the processor in freezing the value is further configured to freeze each value for the at least one parameter if each value for the parameter exceeds the particular confidence level.

13. The system of claim 12, wherein each value of the value set is represented by a plurality of bits, and wherein the processor in computing a likelihood of convergence for each value is further configured to compute the percentage of time a bit has a particular value using values of the bit in previous generations of the genetic algorithm.

14. The system of claim 9, wherein:
the processor in providing signals processed by a plurality of value sets is further configured to:
provide an initial value set to the medical implant system,
provide a first signal to the patient system that is processed by the medical implant system using the provided initial value set, and
provide a second signal to the patient system that is processed by the medical implant system using the provided initial value set; and
the processor in receiving patient feedback is further configured to:
receive patient feedback regarding the provided first signal, and
receive patient feedback regarding the provided second signal.

15. The system of claim 9, wherein the medical implant system is a cochlear implant system and wherein the signals are audible signals.

* * * * *